(12) United States Patent
Liang et al.

(10) Patent No.: US 9,710,414 B2
(45) Date of Patent: Jul. 18, 2017

(54) INTERCHANGEABLE WIRELESS SENSING APPARATUS FOR MOBILE OR NETWORKED DEVICES

(71) Applicant: Ping Liang, Irvine, CA (US)

(72) Inventors: Ping Liang, Irvine, CA (US); Lusha Liang, Irvine, CA (US); Biyonka Liang, Irvine, CA (US)

(73) Assignees: Ping Liang, Newport Coast, CA (US); Lusha Liang, Newport Coast, CA (US); Biyonka Liang, Newpost Coast, CA (US)

( * ) Notice: Subject to any disclaimer, the term of this patent is extended or adjusted under 35 U.S.C. 154(b) by 0 days.

(21) Appl. No.: 14/438,626

(22) PCT Filed: Oct. 26, 2013

(86) PCT No.: PCT/US2013/066989
§ 371 (c)(1),
(2) Date: Apr. 26, 2015

(87) PCT Pub. No.: WO2014/066869
PCT Pub. Date: May 1, 2014

(65) Prior Publication Data
US 2015/0293877 A1    Oct. 15, 2015

Related U.S. Application Data (60) Provisional application No. 61/719,371, filed on Oct. 27, 2012.

(51) Int. Cl.
*G06F 13/00*    (2006.01)
*G06F 13/42*    (2006.01)
*G06F 13/40*    (2006.01)
*A61B 1/00*    (2006.01)
*A61B 1/04*    (2006.01)
(Continued)

(52) U.S. Cl.
CPC ...... *G06F 13/4221* (2013.01); *A61B 1/00016* (2013.01); *A61B 1/00105* (2013.01); *A61B 1/04* (2013.01); *A61B 5/0022* (2013.01); *G06F 13/4068* (2013.01); *A61B 1/227* (2013.01); *A61B 1/24* (2013.01); *A61B 1/303* (2013.01); *A61B 5/0013* (2013.01);
(Continued)

(58) Field of Classification Search
None
See application file for complete search history.

(56) References Cited

U.S. PATENT DOCUMENTS

5,347,307 A *  9/1994  Tanaka ............... G11B 31/006
                                                  348/372
7,477,285 B1 *  1/2009  Johnson ....................... 348/143
(Continued)

*Primary Examiner* — Henry Tsai
*Assistant Examiner* — Dean Phan
(74) *Attorney, Agent, or Firm* — Guosheng Wang; United States Research and Patent Firm (57) ABSTRACT

One embodiment of this invention is an interchangeable sensing apparatus (ISA) comprising a common base unit (CBU), to which a sensor head from a class of sensor heads can be attached using a common or standard interface to produce a sensing apparatus suited for an application, whereas the CBU receives signals from the sensor head and transmits the signals, either through a wired or wireless connection, preferably wireless, to one or more devices.

13 Claims, 4 Drawing Sheets

(51) Int. Cl.
*G06F 3/00* (2006.01)
*H04W 84/12* (2009.01)
*A61B 1/227* (2006.01)
*A61B 1/24* (2006.01)
*A61B 1/303* (2006.01)
*A61B 5/00* (2006.01)
*A61B 5/0402* (2006.01)
*A61B 5/0476* (2006.01)

(52) U.S. Cl.
CPC .......... *A61B 5/0402* (2013.01); *A61B 5/0476* (2013.01); *H04W 84/12* (2013.01)

(56) References Cited

U.S. PATENT DOCUMENTS

| | | | | |
|---|---|---|---|---|
| 2004/0233282 A1* | 11/2004 | Stavely | ............ | G08B 13/19602 348/143 |
| 2005/0083212 A1* | 4/2005 | Chew | .......................... | 340/932.2 |
| 2007/0132849 A1* | 6/2007 | Hill et al. | ...................... | 348/159 |
| 2008/0139881 A1* | 6/2008 | Cover | ................ | A61B 1/00016 600/103 |
| 2012/0206566 A1* | 8/2012 | Fedoseyeva | .................... | 348/38 |

* cited by examiner

INTERCHANGEABLE WIRELESS SENSING APPARATUS FOR MOBILE OR NETWORKED DEVICES

This application claims the benefit of U.S. Provisional Application No. 61/719,371, filed on Oct. 27, 2012.

TECHNICAL FIELD

The present invention relates to interchangeable wireless sensing or imaging apparatus for mobile or networked devices.

BACKGROUND ART

Portable cameras that connect to a computer's USB ports are widely available for many applications, including USB microscope, USB dental camera, USB endoscope, etc. There is also a need to have cameras for these applications that can connect wirelessly to a computer. Because of the wide availability of tablets and smartphones (referred to as mobile devices); most of which do not have USB ports, this need is more prevalent now. There are multiple Wifi (802.11 WLAN) based cameras that attempt to meet this need. However, they suffer several major shortcomings. Prior art wireless cameras are for specific applications and cannot be adapted to different applications by changing the imaging portion and share the common wireless module. Many applications desire a wired or wireless (wireless is often preferred) imaging device whose images (video or pictures) can be viewed on one or more mobile devices or computers either in the same location as or remotely from the imaging device. Examples include digital otoscopes, nasal, throat and other endoscopes for medical applications, dental/intra-oral cameras, microscopes and borescopes, etc. These applications share many common functions and only the imaging sensors or attachments differ in size, shape and/or function. No prior art exploits the common and different elements of these applications to produce products that reduce the cost and increase the convenience for users.

In some prior art, a wireless camera functions as a Wifi Access Point (AP) and a mobile device connects to the AP as a Wifi client. This occupies the Wifi connectivity of the mobile device and the mobile device cannot be connected to the Internet at the same time using Wifi. Moreover, the camera cannot be remotely accessed over the Internet. One prior art solution is to have the camera connect to an external Wifi AP or router (all referred to as AP for convenience) and mobile devices and computers can access the camera via the WLAN or remotely over the Internet if the AP is connected to a wide area network (WAN). This is similar to Wifi surveillance cameras. However, this type of cameras cannot be used in a place that does not have an external Wifi AP, e.g., when students are on a field trip and want to examine wild plant samples, or when a repair person needs to inspect something in the field. There were no wireless cameras that could act both as an AP to mobile devices and a Wifi client to an external Wifi AP, allowing these two kinds of access at the same time.

There is no prior art that possess the functions of the embodiments presented in this invention.

Herein imaging may mean the acquisition of one or more photos or a video stream; an image may mean a digital photo or a video segment. A device may mean a smartphone, a tablet, a notebook or a desktop computer.

SUMMARY OF INVENTION

One embodiment of this invention is an interchangeable sensing apparatus (ISA) comprising a common base unit (CBU), to which a sensor head from a class of sensor heads can be attached using a common or standard interface to produce a sensing apparatus suited for an application, whereas the CBU receives signals from the sensor head and transmits the signals, either through a wired or wireless connection, preferably wireless, to one or more devices. The one or more devices may be devices at the same location as the ISA or at remote location(s) or both. In one embodiment, a sensor head is an imaging head comprising one or more lenses and an image sensor and frontend optics to capture images at desired field of view, resolution and/or magnification appropriate for the application intended by the imaging head, and the shape, size and/or functions of each member of the class of imaging heads are designed to meet the requirement of one or more specific applications. An imaging head may also be equipped with a lens adapter to which different lens assemblies can be attached. An imaging head may include a long extension that may be an electrical cord, a flexible gooseneck or a hard bar with electrical cord inside, where the electrical cord contains wires that connect the imaging signals from an imaging sensor to the CBU. An imaging head may also include a light sources, e.g., one or more LED lights, at the tip which can be switched on to illuminate the scene to be imaged. The light source may be in visible range, or in IR or UV range, polarized, or a combination thereof to capture images illuminated with different frequencies of lights.

DESCRIPTION OF EMBODIMENTS

Reference may now be made to the drawings wherein like numerals refer to like parts throughout. Exemplary embodiments of the invention may now be described. The exemplary embodiments are provided to illustrate aspects of the invention and should not be construed as limiting the scope of the invention. When the exemplary embodiments are described with reference to block diagrams or flowcharts, each block represents both a method step or an apparatus element for performing the method step. Depending upon the implementation, the corresponding apparatus element may be configured in hardware, software, firmware or combinations thereof.

One embodiment is an interchangeable sensing apparatus (ISA) comprising a common base unit (CBU), to which a sensor head from a class of sensor heads can be attached using a common or standard interface to produce a sensing apparatus suited for an application, whereas the CBU receives signals from the sensor head and transmits the signals, preferably through a wireless connection, to one or more devices. The one or more devices may be devices at the same location as the ISA or at remote location(s) or both. A device at the same location as the ISA may connect to the ISA through a wireless local area network (WLAN), e.g., a Wifi connection, with the ISA functioning as an AP or as a client to another WLAN AP. When the ISA is connected to another WLAN AP that is connected to a WAN, devices at remote locations can connect to the ISA over the Internet.

Figure 1:
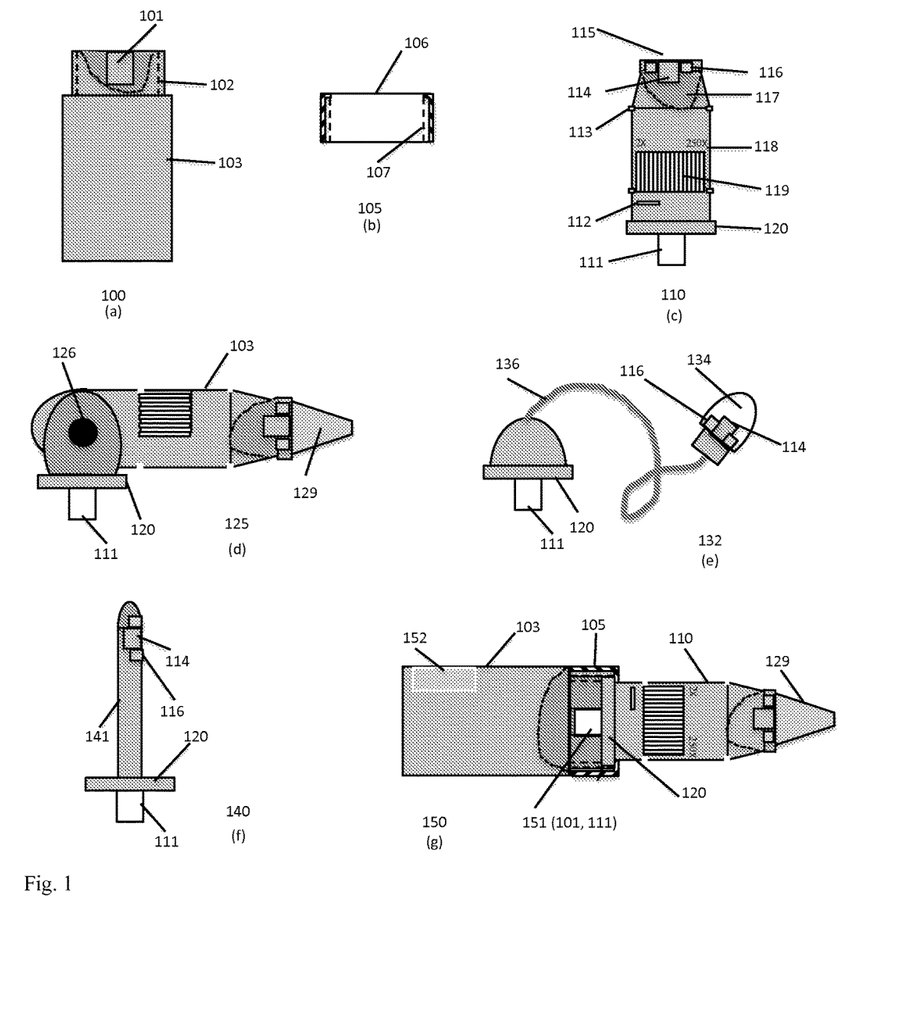
FIG. 1 shows the components and configurations of embodiments of an interchangeable sensing apparatus (ISA), its common base unit (CBU) and various imaging heads.

In one embodiment, a sensor head is an imaging head comprising one or more lenses and an image sensor and frontend optics to capture images at desired field of view, resolution and/or magnification appropriate for the application intended by the imaging head, and the shape, size and/or functions of each member of the class of imaging heads are designed to meet the requirement of one or more specific applications. An imaging head may also be equipped with a lens adapter to which different lens assemblies can be attached. An imaging head may include a long extension that may be an electrical cord, a flexible gooseneck or a hard bar with electrical cord inside, where the electrical cord contains wires that connect the imaging signals from an imaging sensor to the CBU. An imaging head may also include a light sources, e.g., one or more LED lights, at the tip which can be switched on to illuminate the scene to be imaged. The light source may be in visible range, or in IR or UV range, polarized, or a combination thereof to capture images illuminated with different frequencies of lights. Examples of a CBU, several imaging heads, and mechanism for joining an image head to a CBU to form a one-piece ISA are shown in FIG. 1. FIG. 1(a) shows the case of a CBU 100, comprising a base 103 that can be held in hand or attached to a stand, a threaded portion 102 and a plug-in port 102, e.g., a USB port, for receiving a sensor head 110 in FIG. 1(c). When the matching connector 111 of an imaging head 110 is plugged into the receiving port 101, the connecting cap 105 is used to securely join the two pieces 100 and 110 by having the imaging head 110 going through the hole 106, and screwing the cap 105 on to the CBU threaded portion 102 using the matching threads 102 and 107. The cap 105 presses down on the base plate 120 on the imaging head 110 to secure the two pieces 100 and 110 into one unit. Other imaging heads 125, 132, 145 and 300 can be similarly joined to form an ISA. Other parts illustrated in FIG. 1 include an LED light adjustment dial and/or switch 112, slots for attaching accessories 113 (e.g., an imaging head with a dental mirror attachment 160 for imaging teeth and intra-oral, see FIG. 1(h)), lens 114, a place 115 for attaching imaging adapters (e.g., a cone shaped adapter 129 to be used as an otoscope), LED lights 116 shown in the cutout 117 exposing internal parts, numeral marks indicating amplification ratios 118, and a manual focus adjustment wheel 119. Each of the imaging heads may have a manual focus mechanism, a fixed focus, or an auto-focus mechanism. In an embodiment with fixed or auto-focus, the manual focus mechanism may be removed.

FIG. 1(d) shows an embodiment of an imaging head 125 with a rotatable joint 126 so that the imaging head can be rotated to different angles relative to the base 103 for easy imaging. FIG. 1(e) shows an embodiment of an endoscope imaging head 132 with a long flexible or gooseneck cable 136 so that the areas or objects in hard to reach places can be imaged. FIG. 1(f) shows an embodiment of an imaging head 140 with lens 114 and LED 116 facing the side so that it can be used for intra-oral and dental imaging, and for other applications that requires a long reach and imaging sideways. a long flexible or gooseneck cable so that the areas or objects in hard to reach places can be imaged.

FIG. 1(g) shows how an imaging head, using 110 with an otoscope adapter 129 as an example, is joined with a CBU 100 by the matching plug-in connectors 101 and 111 and secured by the cap 107.

FIG. 1(h) shows how an imaging head 110 with an attachment mechanism 163, e.g., clip-on or snap-on, that has an adjustable holder 164 (e.g., a clip that can be opened to different width, or through-hole that can be squeezed by tightening a screw mechanism) that can hold a dental mirror or laryngeal mirror 161 of different thickness handles 162 for inspection of oral cavity, teeth or throat. In yet another embodiment, the CBU 100 is equipped with a built-in display screen, e.g., an LCD screen 171, as shown in FIG. 1(i) mounted on a CBU 100. FIG. 1(i) shows such an embodiment 170 with an otoscope adapter. In such an application, ear drum images can be shown on the display, such that the person holding the imaging apparatus can see the images directly on the apparatus and other people can see the images on a separate device via a wireless link in a local area network, or remotely over the Internet. In an application example, a doctor may see the ear canal of a patient on the LCD screen on the common base unit, while the doctor let the patient or patient's family member(s) see the same images on a separate device. In yet another embodiment, the CBU has a holder that can hold a separate first device, e.g., a smartphone, and the images are wirelessly transmitted to the first device and shown on the screen of the first device. In another embodiment, the holder is adjustable, e.g., in width, length and height, and has a tightening mechanism, e.g., using one or more disks that can be screwed down to press on a first device, for the purpose of allowing a variety of separate first devices to be held onto the CBU or ISA.

The sensor chip and/or sensor frontend in a sensor head or imaging head may be different for different applications, e.g., for a digital microscope, the sensor frontend may include optics for magnification of object and LED lighting; for a standard microscope; the sensor frontend includes a standard mount, e.g., C-mount for attaching to a camera viewport of a standard microscope; for an otoscope, the frontend includes lighting and an adapter 129 or guide for inserting into the ear canal; for an intraoral camera, the frontend includes lighting and side-mounted lens or reflective mirror at one end of a long thin neck for insertion into a mouth to capture images of teeth or throat that can be orthogonal to the neck of the imaging head; for a borescope or endoscope, the sensor and frontend are attached to one end of a long flexible cable or gooseneck 136 that carries the signal or data from the sensor chip to the plug-in connector for transmission to the CBU. In each case, an imaging head may include a dial or switch 112 that the can adjust the intensity of the light, or turn on and off the light, based on the need of the application, as illustrated in FIG. 1(c).

Figure 2:
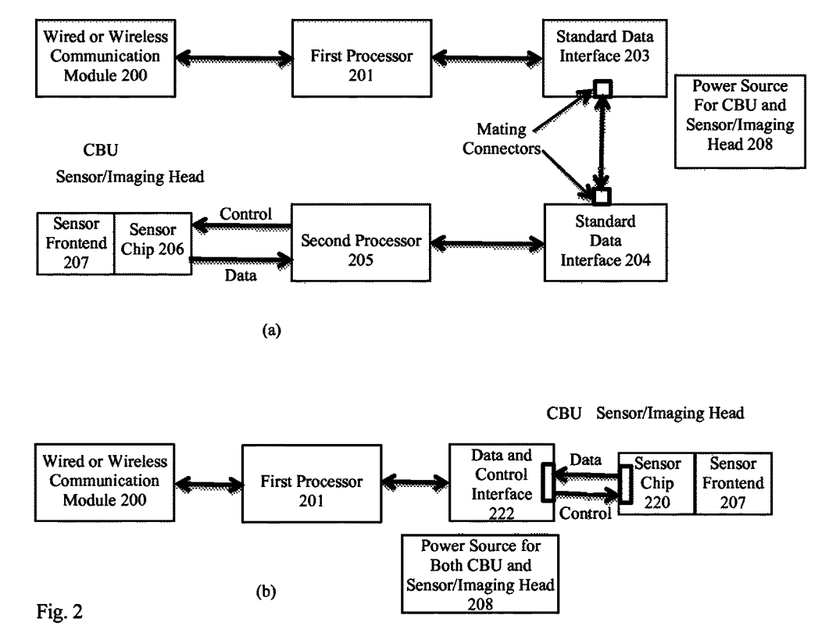
FIG. 2 shows the block diagrams of embodiments of an ISA.

The common base unit CBU, as shown in FIGS. 1(a) and 2, comprises a first processor 201 for receiving data from a sensor or imaging head via a data interface, a wired or wireless communication module 200 coupled to the first processor whereas under the control of the first processor 201, the communication module 200 transmits the signals or images over a wired or wireless link to one or more devices, and a power source 208, e.g., a battery, or a port for connection to an external power supply source, or both. The preference is a rechargeable battery to allow complete wireless operation of the ISA, and recharging of the battery when needed. The CBU can be made into a shape and size that is easy and comfortable for holding with one hand so that the ISA can be used as a handheld sensing or imaging device. The block diagrams of two embodiments are shown in FIG. 2, which show the block diagram of the CBU on one side of the dashed line, and the block diagram of the sensor or imaging head on the other side of the dashed line. FIG. 2(a) shows an embodiment where the CBU and a sensor head or imaging head are connected via a standard matching data interface 203 and 204, e.g., USB male and female connectors, and a second processor 205 in the sensor or imaging head receives data from the sensor or imaging chip 206, processes the data if necessary, and transform the data into the electrical format and connected to the mechanical format as required by the standard data interface 204 to transmit the data to the standard data interface module 203 in the CBU. FIG. 2(*b*) shows an embodiment where the CBU and a sensor head or imaging head are connected directly via the data and control interface 222 of the sensor or imaging chip 223. In both embodiments, the power source 208 supplies power to both the CBU and the sensor or imaging head, which may require the inclusion of power wires in the plug-in connectors between the CBU and the sensor or imaging head. In FIG. 2(*a*), the standard data interface 203 and 204 may already include the power wires, e.g, as in the USB standard. The advantage of the embodiment in FIG. 2(*a*) is that many sensor or imaging sensors can be easily interfaced with a common CBU because the second processor and standard data interface in the sensor or imaging head translates the data into the standard data interface used by the CBU and the physical connectors are also standard. The advantage of the embodiment in FIG. 2(*b*) is the lower cost as less chips are needed. However, the interchangeable sensor or imaging heads for a CBU must use only sensor or imaging sensor chips that have the same data and control interface between 222 and 223.

In one embodiment, a CBU is coupled with an input device either wired or wirelessly, preferably wireless, and the CBU can be configured or a command can be entered into the CBU through the input device. The input device may be a wired or wireless (e.g., Bluetooth) keypad or keyboard, or a device with processor, a screen and input means (e.g., a smartphone or tablet coupled to the CBU via Bluetooth, or a computer coupled to the CBU via USB). In this case, a graphic UI may be displayed on the screen of the coupled device and CBU configuration, command or status can be entered, viewed and selected/deselected in the graphic UI.

In another embodiment, a CBU or ISA includes a network-mode-select switch to switch the CBU to function as a wireless Access Point (AP) (e.g., 802.11 b/g/n WLAN AP) or as a client to a wireless AP. In yet another embodiment, a CBU may also be configured to function in an ad-hoc mode to connect with one or more devices in a peer-to-peer connection. The network-mode-select switch may be implemented using a physical switch on the CBU or ISA, a virtual on-screen switch on the CBU or ISA, or as a checkbox in a UI on a coupled input device which transmits the selection/dis-selection on the UI to the CBU, or a command entered into the CBU via an input device coupled with the CBU either wired or wirelessly.

When a user is using an ISA of this invention in a place without a WLAN AP, the CBU can be configured or switched to function as a WLAN AP and device(s), e.g., smartphone or tablet, can connect to this AP as clients of the CBU AP and the signals or images from the ISA can then be viewed or streamed to or captured on the connected device(s). In one embodiment, a device connected to the CBU AP that has a wireless wide-area network (WWAN) connection, e.g., a 3G, 4G LTE, or WiMax network, or their successors, runs an app on the device to transmit the signals or images to one or more remote devices via the WWAN connection.

Having the CBU function as a WLAN AP provides the advantage that local device(s) can easily discover the CBU AP and connect to it. However, its limitations are that a device connected to the CBU AP will no longer be able to use the same WLAN module to connect to the Internet, and a remote device is unable to directly connect to the CBU AP. One embodiment overcomes this by having the CBU functions as a WLAN bridge so that it can wirelessly connect to a first WLAN router that is connected to the Internet via a wired connection (e.g., Ethernet, cable modem, or fiber, WWAN) and serves as a WLAN AP for the devices connected to the CBU. One embodiment implements this by time division of a single WLAN radio. Another embodiment implements this by using two WLAN radios (e.g., two 802.11 b/g/n modules) so that one can connect to the first WLAN router and the other can serves as a second WLAN AP for connections with devices viewing/capturing signals or images from the ISA. As a result, a mobile device that is connected to the second WLAN AP can view/capture images from the CBU/ISA and at the same time connect to the Internet using WLAN by having the CBU processor bridge the data between the second WLAN module (for serving as an AP to mobile device(s)) and the first WLAN module (connected to the first WLAN router).

In another embodiment, when a user is using an ISA of this invention in a place with a first WLAN AP, the CBU can be configured or switched to function as a wireless client to the first WLAN AP. When the CBU is configured or switched to function as a wireless client to the first WLAN AP, the CBU runs a web server or an image or video streaming server and one or more devices in the same WLAN can connect to the server on the CBU using its IP address or URL via a dynamic DNS (DDNS) service to view or capture the signals or images from the ISA. One embodiment includes an app running on a device in the same WLAN that automatically discovers the IP address of the CBU and connect to the ISA. The CBU may broadcast a message that the app can recognize to facilitate the auto-discovery of the IP address of the CBU. A DDNS service may be used to provide a dynamic DNS service so that a remote Internet-connected device can access the ISA using a URL that will be translated by the DDNS into the IP address (an port number if there is one) of the CBU. One or more remote devices can then use the URL to access the server running on the CBU to view or capture the signals or images from the ISA.

In another embodiment, a CBU or ISA is configured by software or firmware to be able to switch between functioning as a wireless AP (e.g., 802.11 b/g/n WLAN AP) or as a client to a wireless AP, without the need of a switch to change its mode of operation. In one implementation, upon powering on or awake from sleep, the software or firmware causes the CBU or ISA to function alternately (1) as a client connected to another WLAN AP and (2) as a WLAN AP which broadcasts its own WLAN SSID so that other devices can detect the SSID and accepts other device's connection as a client of the CBU or ISA'a WLAN AP. When a device chooses to use the CBU or ISA as a WLAN AP, the software or firmware running in the CBU or ISA automatically recognize the connection and have the CBU or ISA function as a WLAN AP; and when a device chooses to treat the CBU or ISA as a client of another WLAN AP, the software or firmware running in the CBU or ISA automatically recognize the connection and have the CBU or ISA function as a client of that WLAN AP. With this embodiment, no network-mode-select switch is needed. A CBU or ISA functions as a WLAN AP or a client to a separate WLAN AP as needed.

In yet another embodiment, a CBU or ISA is configured by software or firmware to be able to function as a wireless AP (e.g., 802.11 b/g/n WLAN AP) and as a client to a wireless AP using time-division, whereas the software or firmware causes the CBU or ISA to function alternately (1)

as a client connected to another WLAN AP and (2) as a WLAN AP which broadcasts its own WLAN SSID so that other devices can detect the SSID and accepts other device's connection as a client of the CBU or ISA'a WLAN AP. As a result, a device can function as a WLAN client and request connection to the CBU or ISA and the software or firmware running in the CBU or ISA automatically recognizes the connection request and have the CBU or ISA function as a WLAN AP to the device so that the device can receive signals or images from the CBU or ISA; and when a device chooses to treat the CBU or ISA as a client of another WLAN AP by requesting data from a port on the CBU or ISA, the software or firmware running in the CBU or ISA automatically recognizes the connection and have the CBU or ISA function as a client of that WLAN AP. With this embodiment, no network-mode-select switch is needed. A CBU or ISA functions as a WLAN AP or a client to a separate WLAN AP as needed. It may function both as a WLAN AP to one or more devices and as a client to another WLAN AP using time division.

When access to the ISA is provided to one or more remote devices, several means can be used to protect the privacy of the user, including using a password, special URL or an allow-remote-access switch, or a combination thereof. When remote access is controlled using a password and an easy to remember or a special URL, it may be further limited by time, functions allowed, number of times accessed, IP, or a combination thereof. In one embodiment, an allow-remote-access switch is used to control the allowance of remote access, a remote device is allowed to access the signal or images provided by the server running on the CBU only when this switch is turned on. The allow-remote-access switch may be implemented using a physical switch on the CBU or ISA, a virtual on-screen switch on the CBU or ISA, or as a checkbox in a UI on a coupled device which transmits the selection/dis-selection on the UI to the CBU, or a command entered into the CBU via an input device coupled with the CBU either wired or wirelessly. In one embodiment, a password and an easy to remember URL or a special URL is used to allow remote devices to access an ISA and the allow-remote-access switch controls when remote access is allowed. In another embodiment, a time limited password (to be used with a long term easy to remember URL) or a special URL is generated each time the allow-remote-access switch is pressed. The user of the ISA provides the password and long term URL or the time-limited URL (e.g., https://limited-Access-Code-here.ISAserver.com) to a remote user to allow him to access the signal or images from the ISA. To facilitate this process, the CBU can be configured such that when the allow-remote-access switch is pressed, the password and long term URL or the time-limited URL is automatically sent to one or more specified destinations via a message or email or other means, for example, shown in a window of an app running on a device linked with the ISA for viewing the signals or images from the ISA, or sent to a remote user's email or message inbox, or sent to the ISA user's email or message inbox who can then forward or copy-paste and send the information to a remote user to allow access. The ISA's user can log in as an administrator and edit the destination(s) to which the access information is sent. In another embodiment, when the allow-remote-access switch is pressed, the password and long term URL or the time-limited URL is shown on a display, e.g., an LCD screen 152 on the CBU or ISA as shown in FIG. 1(g). In yet another embodiment, a user enters a limited access password or URL into the CBU using an input device coupled to the CBU or ISA wired or wirelessly, or using an app running on a device (linked to the CBU or ISA) that provides a UI to let the user enter a limited access password or URL into the CBU. In either case, the user can then send the information to a remote user. In the case of using the UI of an app to enter a limited access password or URL into the CBU, the app can record and send the limited access password or URL to a specified remote user.

In one embodiment, the electrical coupling between a sensor head and a CBU uses a common or standard interface as shown in FIG. 2(a), e.g., USB, Thunderbolt, HDMI, or other present or future data interfaces, in which a second processor and a controller of the standard interface in a sensor head or imaging head converts the signal or data from the sensor into the format of a data interface standard and communicates with a CBU to transfer the data to the CBU. An standard interface or a serial interface that also supplies the power to the sensor head or imaging head, such as USB, is preferred as it reduces the number of electrical connections and not only standardizes the data connection but also provide the power connection. The advantages of the this embodiment are (1) it allows many different types of sensors with different parallel or serial data output interfaces and control interfaces or different analog to digital conversion parameters, such as CMOS or CCD image sensors of different resolution and interfaces, multichannel ECG or EEG sensors, or any other input or output (I/O) device with the same standard interface, to be electrically coupled to the CBU using a common or standard interface, e.g., USB, Thunderbolt, Thunderbolt, HDMI, or other present or future data interfaces, thus, with the installation of the required driver(s), allowing the same CBU to provide its networking functions to a wide variety of sensor heads, imaging heads, or other I/O devices, e.g, USB cameras for standard microscopes, USB web cams, and (2) a sensor head or imaging head can also be coupled with a first device directly using the common or standard interface, e.g., connected to a computer's USB, Thunderbolt, HDMI, or other present or future data interface port using a cable of that standard, to provide the sensing or imaging functions to the first device. In the case the standard interface is USB or other interfaces that supports Human Interface Devices (HID), an input device such as a keyboard or a composite device with an input device and a display screen that uses the same standard interface can be connected to the CBU to change or set its configurations or parameters.

In addition to facilitate the coupling with a wider variety of sensor heads and I/O devices, the use of a standard interface such as USB also enables a new class of independent embodiments in which the exchangeability of different sensor heads is not a necessary feature. One embodiment of this invention is a sensing apparatus (ISA) comprising a sensor head that can be connected using a standard data and power interface either (1) to a base unit (still referred to for short as a CBU for convenience but with the understanding that having the base unit serve as a "common base unit" for a class of sensor heads is not a necessary feature of this embodiment) and mechanically joined with the CBU to produce a one-piece sensing apparatus, e.g., a one-piece handheld wireless imaging apparatus without wires from or to external connections, or (2) to another device, such as a computer or a mobile device with a port of the same standard, using the same standard data and power interface through a cable of that standard, to function as a peripheral to the device, e.g., as an USB camera.

Figure 3:
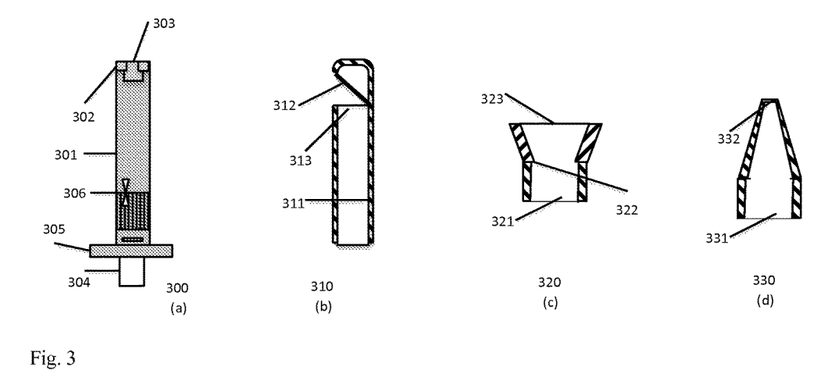
FIG. 3 shows the components and attachments of another embodiment imaging head.

Another embodiment is a multi-use sensing or imaging apparatus comprising a base unit that includes a first processor for receiving data from a sensor or imaging head and for transmitting signals or images through a wired or wireless link to one more devices, a wired or wireless communication module coupled to the first processor whereas under the control of the first processor, the communication module transmits the signals or images over a wired or wireless link to the one or more devices, and a self contained power source, e.g., a battery, or a port for connection to an external power supply source, or both; a sensor head or an imaging head that includes one or more lenses and image sensor whereas the sensor head or imaging head may be attached to, through a connector, or integrated with the base unit; and a class of interchangeable adapters that are to be attached to the tip of the imaging head 300 in FIG. 3(a), where the attachment of an adapter converts the whole apparatus into an imaging apparatus suited for a specific application as shown in FIG. 3. Examples of interchangeable adapters are illustrated in FIGS. 3(b)-(d), including a funnel shaped adapter 330 for insertion into an ear canal for the integrated imaging apparatus to function as an otoscope FIG. 3(d), a cone shaped adapter 320 to provide a distance between the objective lens and object to be imaged for the integrated imaging apparatus to function as a microscope FIG. 3(c), a long sleeve adapter 310 with a reflector 312 to reflect the image into the image sensor FIG. 3(b) for use as an intra-oral or dental camera, where multiple long sleeve adapters can be sterilized or disinfected so that a clean one can be used for each patient. The long sleeve adapter in FIG. 3(b) may also include a lens, lights (e.g., surface mount LEDs) around the lens and electric conductors to couple electric power to the lights for the integrated imaging apparatus to function as a dental or intra-oral camera with a wider magnified field of view. The above multi-use imaging apparatus can be made into a shape and size that is suitable for a handheld device. Furthermore, the imaging head and the base unit may be joined by a rotatable joint so that the imaging head can be angled to better image a target.

An imaging head may have a manual focus or an auto focus mechanism. In some applications, a fixed focus setting may be desired so that the images are always in focus as long as the lens is a certain distance away from the object being imaged, e.g., for viewing teeth inside a mouth. In one embodiment, a special setting is provided on an imaging head to set the focus into a fixed focus, e.g., one or two markers 306 on a manual focus imaging head where the alignment of the two markers puts the focus into a fixed setting for viewing objects from a fixed distance as shown FIG. 3(b), or a button or switch on an auto focus imaging head where the press of the button or switch turns off auto focus and puts the focus into a fixed setting for viewing objects from a fixed distance.

In one embodiment, image or video compression is performed in the first processor in the CBU before wired or wireless transmission to other devices, in another embodiment, image or video compression is performed in a processor in an imaging head before transmission over the electrical coupling to the CBU.

When a CBU and a sensor or imaging head is mechanically and electrically coupled into one piece with the CBU functioning as a handle, the whole apparatus becomes a handheld imaging apparatus suited for the application intended by the coupled imaging head. Changing the imaging head changes the apparatus to be suited to a different application. Examples of imaging heads are:

Optical and image sensor components and a first extension for inserting into an ear canal for imaging inside the ear so that whole apparatus functions as a wireless and network accessible imaging otoscope, (FIGS. 1(d), 1(g), 1(i) and 3(d))

Optical and image sensor components and a first extension inserting inside an open mouth for intra oral imaging, so that when the whole apparatus functions as a wireless and network accessible imaging as a dental, intra-oral or throat check-up camera, (FIGS. 1(f), 1(h) and 3(b))

Optical and image sensor components and a first extension for inserting into a nasal passage for imaging inside the nose so that whole apparatus functions as a wireless and network accessible imaging nasal passage check-up camera, (FIGS. 1(d), 1(g) and 3(d))

Optical and image sensor components and a first flexible extension for inserting into a trachea, colon or an esophagus and the stomach, so that the whole apparatus functions as a wireless and network accessible imaging medical endoscope, (FIG. 1(e))

Optical and image sensor components and a first flexible or hard extension for inserting inside a machine, into a hard to reach place or a confined space (e.g., through an opening to the inside of the hollow portion of an object, a drain pipe, an air vent, etc.), so that the whole apparatus functions as a wireless and network accessible imaging inspection borescope, (FIG. 1(e))

Optical and image sensor components and a first flexible or hard extension for extending out a hiding place or around a corner for imaging a scene or activity while staying out of the line of sight of the target to be imaged so that the whole apparatus functions as a wireless and network accessible spying camera, (FIG. 1(e))

A magnifying, zooming or telescoping lens assembly and image sensor components so that the whole apparatus functions as a wireless and network accessible imaging handheld microscope (for industrial inspections of biological samples, printed circuit boards, materials such as fabric, wood, synthetic materials, etc. or joints that connect two or more pieces such as welding, soldering, etc.), zooming or telescoping camera. (FIGS. 1(c) and 3(c))

Image sensor components and a mount for attaching to a viewport of a microscope or image sensor components in a cylindrical enclosure that be inserted into a viewport of a microscope so that the images from the microscope can be streamed to devices in a local network and/or viewed remotely over a network.

In the above embodiments, the first extension may be of a certain length and flexibility as required for the intended application, and the imaging optics and sensor can be mounted at the tip of a long, flexible first extension, and a control mechanism that can bend or guide the imaging tip and the first extension through a canal, passage or confined space, as required in some endoscopic applications in medicine and in borescopic applications. In another embodiment, an imaging head includes at the tip a mechanism that can open up or clear up the surroundings. This embodiment is useful for endoscopic applications in medicine for opening up passages, e.g., stretching open a nasal passage, to better imaging the passage, or to clear away obstacles, e.g., clear away remnants inside a colon in colonoscopy, or clear away debris in a confined or hidden space a borescopic application.

In one embodiment, the battery for a CBU is made into an interchangeable attachment so that a different size battery can be attached to the CBU suited for the application at hand, lighter weight for some applications, longer lasting for other applications.

In many applications, it is desired that signals or images from two or more samples are compared side by side. One embodiment includes an app that is running on a device and can connect to two or more ISAs and displays signals or images from two or more ISAa side by side. The CBUs of the two or more ISAs can be configured to connect as clients to a common AP, and the viewing device is also connected as client to the same AP. The app can then access the two or more ISAs through their individual URLs and displays the two or more signals or images side by side on the screen of the device, enabling a user to compare the signals or images. In another embodiment, an app that is running on a device and can connect to one or more ISAs and displays side by side signals or images from one or more ISAa and one or more signals or images stored on the device or located at another location on the network through its or their individual URLs. Both the CBU(s) of the one or more ISAs can be configured to connect as client(s) an AP, and the viewing device is also connected as client to the same AP. The app can then access the one or more ISAs through their individual URLs and displays the one or more signals or images from the ISA(s) side by side with the one or more signals or images stored on the device or located at another location on the network through its or their individual URLs, enabling a user to compare the signals or images. The embodiment of an app on a device that can display images from multiple signal or imaging sensors side by side can be extended to beyond ISA. Each of the ISA in this embodiment can be replaced by any communication module that transmit signals or images from its coupled signal or imaging sensor, either via a wired or a wireless channel, that can be received by a common viewing device.

In one embodiment as a portable and network accessible signal collection apparatus, a sensor head is a signal collection or acquisition device that collects one or more channels of signals, e.g., ECG or EEG signals, other physiological signals from a living being, or physical signals from a physical or chemical or natural process, and the CBU can be of a shape and size appropriate for the application, e.g., as a tabletop stand, box-shaped with a clip or hanging strap for attaching to a piece of clothing or worn by a person whose physiological signal(s) is being collected. In another embodiment, a sensor head is electrically coupled to a CBU, and not necessarily tightly attached mechanically.

The medical use of this invention, including otoscope, intra-oral camera, nasal camera, anal or vaginal camera, various other medical endoscopes, microscope, and the portable and network accessible ECG, EEG or other physiological signal collection apparatus, allows real-time remote consultation or diagnosis by a doctor or medical expert(s), where patient is at home or a remote location.

As an extension to the above embodiments, one embodiment is an adapter with one coupling for connecting to an optical or lens assembly and illumination light source and an adjustable coupling with a tightening mechanism, e.g., using one or more disks that can be screwed down to firmly attach the adapter to a first mobile device, e.g., a smartphone, whereas the optical or lens assembly will project an image to the camera of the first mobile device and the adjustable coupling with a tightening mechanism can be adjusted, e.g., in width, length and height, to be attached to a variety of first mobile devices. There are prior art adapter for coupling a lens assembly, e.g., zooming lens, to a smartphone, but they are specific to each smartphone, e.g., only works for an iPhone 4, or a Galaxy Nexus S. This embodiment allows a single adapter to be used with a variety of mobile devices.

One embodiment remote viewing microscope comprises a microscope with a focus mechanism that can be remotely controlled either via a wired or wireless communication channel that receives commands from a user, an imaging sensor coupled to the microscope to capture the images seen by the microscope; a first processor that is coupled to the image sensor and receives data from the imaging sensor; a wireless communication module coupled to the first processor whereas under the control of the first processor, the communication module transmits the signals or images over a wireless link to the one or more mobile devices such as tablet computers or smartphones; a self contained power source, e.g., a battery, or a port for connection to an external power supply source, or both; and a robotic arm that can move samples under or away from the objective lens of the microscope and the robotic arm can be remotely controlled either via a wired or wireless communication channel that receives commands from a user. This embodiment allows one or more users to inspect samples using the microscope and a mobile device while not being physically next to the microscope. This is especially useful for inspecting dangerous samples such as viruses, bacteria, radioactive materials, etc.

Although the foregoing descriptions of the preferred embodiments of the present inventions have shown, described, or illustrated the fundamental novel features or principles of the inventions, it is understood that various omissions, substitutions, and changes in the form of the detail of the methods, elements or apparatuses as illustrated, as well as the uses thereof, may be made by those skilled in the art without departing from the spirit of the present inventions. Hence, the scope of the present inventions should not be limited to the foregoing descriptions. Rather, the principles of the inventions may be applied to a wide range of methods, systems, and apparatuses, to achieve the advantages described herein and to achieve other advantages or to satisfy other objectives as well.

What is claimed is:

1. An interchangeable sensing apparatus comprising a common base unit which comprises:
   a first processor, a wireless communication module and a first interface;
   a power supply; and
   a sensor head selected from two or more sensor heads;
   wherein the sensor head is connected to the common base unit using the first interface that is a data and power interface, and mechanically joined with the common base unit using a matching plug-in connector to produce a one-piece apparatus without wires from or to external connections;
   wherein each of the two or more sensor heads performs a distinctively different function and is configured to connect to the common base unit to produce a one-piece networking sensing apparatus suited for an application; and
   wherein the sensor head comprises a chip for signal collection or generation and a matching interface to the first interface and the signals from the chip is transmitted to or received from the first processor in the common base unit via the matching interface, and the wireless communication module under the control of the first processor, transmits the signals to or receives the signals from one or more devices wirelessly, wherein said one or more devices are users' viewing devices that display an image received from the wireless communication module, wherein the common base unit further comprises both a first WLAN access point function to connect one or more devices to it as WLAN clients and a WLAN client function to connect to a second WLAN access point or router so that a first set of one or more local devices receive signals directly from the interchangeable sensing apparatus as WLAN clients to the first WLAN access point and concurrently using time division, a second set of one or more devices receive signals from the interchangeable sensing apparatus via the second WLAN access point or router, whereas the second set of one more devices include one or more local devices, and if the second WLAN access point or router is connected to a wide area network, the second set of one more devices include one or more remote devices connected to the interchangeable sensing apparatus via the second WLAN access point or router over the Internet.

2. The interchangeable sensing apparatus in claim 1, which is a handheld apparatus, wherein the first interface is a USB interface of one gender in the common base unit and the matching interface in the sensor head is a USB interface of the opposite gender, and the power to the sensor head is supplied by the common base unit via the USB interface.

3. The interchangeable sensing apparatus in claim 1, wherein the two or more sensor heads include at least two different types of image sensor heads each for a distinctively different sensing function, and wherein one of the two or more sensor heads is a microscope, an otoscope, an intraoral camera, a borescope, or an endoscope.

4. The interchangeable sensing apparatus in claim 1, further comprising one or more adapters to connect the sensor head to a second apparatus to provide a means to capture the signal or image digitally from the second apparatus.

5. The interchangeable sensing apparatus in claim 1, wherein the two or more sensor heads further include a sensor head with a rotatable joint so the sensor head can be rotated relative to the common base unit.

6. The interchangeable sensing apparatus in claim 1, wherein the two or more sensor heads are further configured to connect directly to an I/O port on a computer using a cable via the matching interface to the first interface and transmits signals from the chip for signal collection or generation to the computer, without the use of the common base unit.

7. The interchangeable sensing apparatus in claim 1, wherein the common base unit further comprises both a first WLAN access point function to connect one or more devices to it as WLAN clients and a WLAN client function to connect to a second WLAN access point or router; and further comprises a hardware or virtual switch that is used to switch the common base unit to the first WLAN access point function or to the WLAN client function.

8. The interchangeable sensing apparatus in claim 1, further comprising a hardware or virtual switch that is used to allow or disallow remote access to the interchangeable sensing apparatus.

9. The interchangeable sensing apparatus in claim 1, further comprising an attachment mechanism that allows a larger battery to be attached as power supply for longer battery-operated running time and a smaller battery to be attached as power supply for smaller size and convenience.

10. A method of wireless sensing, which comprises the steps of:
   selecting a sensor head from two or more sensor heads, wherein each of the two or more sensor heads performs a distinctively different function, and the sensor head comprises a chip for signal collection or generation and a matching interface to a first interface,
   connecting the sensor head to a common base unit using the first interface that is a data and power interface, and mechanically joining the sensor head with the common base unit using a matching plug-in connector to produce a one-piece apparatus without wires from or to external connections, wherein the common base unit which comprises a first processor, a wireless communication module and the first interface and a battery as a power supply,
   wherein the head sensor transmits signals from the chip and receives signals from the first processor in the common base unit via the matching interface and the wireless communication module under the control of the first processor, and transmits signals to or receives from one or more devices wirelessly, wherein said one or more devices are users' viewing devices that display an image received from the wireless communication module, and
   connecting one or more devices to the common base unit using a First WLAN access point function as WLAN clients and connecting the common base unit to a second WLAN access point or router using a WLAN client function so that a first set of one or more local devices receive signals directly from the wireless sensing apparatus as WLAN clients to the first WLAN access point, and concurrently using time division to transmit signals from the wireless sensing apparatus to a second set of one or more devices via the second WLAN access point or router, whereas the second set of one more devices includes one or more local devices, and if the second WLAN access point or router is connected to a wide area network, the second set of one or more devices include one or more remote devices connected to the wireless sensing apparatus via the second WLAN access point or router over the Internet.

11. The method in claim 10, further comprising:
using a user interface on a mobile device to configure the wireless communication module, or other settings in the common base unit or in a sensor head.

12. The method in claim 10, further comprising:
providing a secure authentication of one or more remote users and a remote user interface for one or more remote user to view signals from the wireless sensing apparatus after authentication via the Internet.

13. The method in claim 10, further comprising:
providing a user interface that can accept signals from two or more wireless sensing apparatuses and display them side by side for comparison.

* * * * *